United States Patent
Losso et al.

(10) Patent No.: US 7,109,300 B2
(45) Date of Patent: Sep. 19, 2006

(54) EXTRACTION OF COLLAGEN FROM CALCIFIED TISSUES

(75) Inventors: Jack N. Losso, Baton Rouge, LA (US); Masahiro Ogawa, Kagawa (JP); Ralph J. Portier, Baton Rouge, LA (US); Mark A. Schexnayder, Metairie, LA (US)

(73) Assignee: Board of Supervisors of Louisiana State Univeristy And Agricultural and Mechanical College, Baton Rouge, LA (US)

( * ) Notice: Subject to any disclaimer, the term of this patent is extended or adjusted under 35 U.S.C. 154(b) by 112 days.

(21) Appl. No.: 11/108,594

(22) Filed: Apr. 18, 2005

(65) Prior Publication Data

US 2005/0267292 A1    Dec. 1, 2005

Related U.S. Application Data

(60) Provisional application No. 60/563,439, filed on Apr. 19, 2004.

(51) Int. Cl.
  C07K 14/78   (2006.01)
  A61K 38/17   (2006.01)
  A23J 1/00    (2006.01)

(52) U.S. Cl. ............... 530/356; 530/423; 530/427; 514/21

(58) Field of Classification Search ......... 530/356; 424/549
See application file for complete search history.

(56) References Cited

U.S. PATENT DOCUMENTS

| 5,331,092 A | 7/1994 | Huc et al. ............. 530/356 |
| 5,420,248 A | 5/1995 | Devictor et al. ....... 530/356 |
| 5,698,228 A | 12/1997 | Takai et al. ........... 424/549 |
| 5,703,211 A | 12/1997 | Taylor ................. 530/356 |
| 6,271,350 B1 | 8/2001 | Shimizu et al. ....... 530/356 |

FOREIGN PATENT DOCUMENTS

EP    1 270 672    1/2003

OTHER PUBLICATIONS

Kim, J. et al, "Application of ozone for enhancing the microbiological safety and quality of foods: a review," *J. Food Prot.*, vol. 62, pp. 1071-1087 (1999) (abstract).

Losso, J. et al., "Two value-added products from Louisiana seafood processing facilities," Louisiana Agriculture, pp. 11-12 (Fall 2002).

"LSU researchers may create new industry from fish waste," Sunday Advocate (Baton Rouge, LA), p. 41 (Apr. 20, 2003).

Ogawa, M. et al., "Bone and scale collagens from subtropical fish black drum and sheepshead seabream: biochemcial and thermal (physicochemical) properties," submission to Food Chemistry or International Journal of Biological Macromolecules (2003).

(Continued)

*Primary Examiner*—Karen Cochrane Carlson
*Assistant Examiner*—Marsha Tsay
(74) *Attorney, Agent, or Firm*—John H. Runnels; Bonnie J. Davis; André J. Porter

(57) ABSTRACT

A method is disclosed for extracting collagen from calcified tissue without a prior decalcification step. The method may be used with calcified tissues such as fish skin with scales, alligator skeletons, and crustacean exoskeletons. It does not require the use of EDTA. When fish skin is used that contains substantial quantities of scales, it is not necessary first to remove scales from the skin before conducting the extraction of collagen.

16 Claims, 1 Drawing Sheet

OTHER PUBLICATIONS

Ogawa, M. et al., "Biochemical properties of black drum and sheepshead seabream skin collagen," J. Agric. Food Chem., vol. 51, pp. 8088-8092 (2003).

Ogawa, M. et al., "Biochemical properties of bone and scale collagens isolated from the subtropical fish black drum (*Pogonia cromis*) and sheepshead seabream (*Archosargus probatocephalus*)," Food Chemistry, vol. 88, pp. 495-501 (2004).

Ogawa, M. et al., "Biochemical properties of collagen from skin of Gulf coast fish," Abstract 76A-33, presented at Annual Meeting of the Institute of Food Technologists (Chicago, IL, Jul. 12-16, 2003).

Wood, A. et al., "Biochemical properties of Alligator Mississippiensis Bone," Summer Undergraduate Research Forum Paper #95, Louisiana Biomedical Research Network, (Baton Rouge, LA, Jul. 31, 2003).

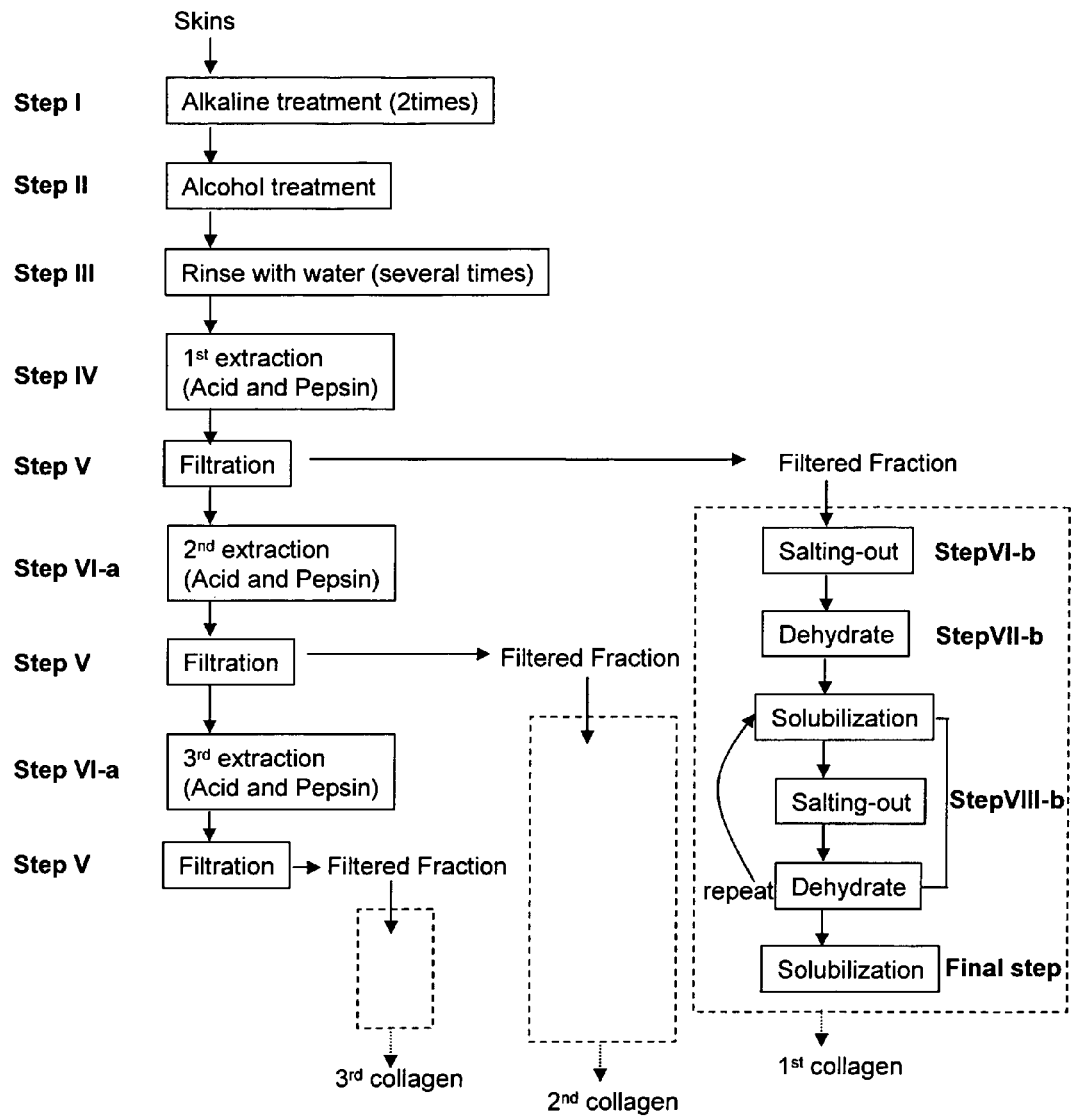
FIGURE

EXTRACTION OF COLLAGEN FROM CALCIFIED TISSUES

The benefit of the Apr. 19, 2004 filing date of provisional application Ser. No. 60/563,439 is claimed under 35 U.S.C. § 119(e).

The development of this invention was partially funded by the United States Government under grant number 167-14-5114 from the National Oceanic and Atmospheric Administration (Sea Grant). The United States Government has certain rights in this invention.

This invention pertains to the extraction of collagen from calcified tissue, for example fish skin with scales, alligator skeletons, chicken skeletons, turkey skeletons, and crustacean shells; particularly where the extraction of collagen is not preceded by decalcification of the calcified tissue.

Collagen is the most abundant protein in most vertebrates, constituting about a quarter of the total protein found in many species. Collagen comprises insoluble fibers that have a high tensile strength, and that are distinguished by a right-handed triple superhelical rod comprising three, nearly-identical polypeptide chains. Collagen and collagen peptides (subunits) are widely used in such areas as food, cosmetics, pharmaceuticals, glue, and photography. The principal raw materials that are currently used as sources for generating collagen commercially are bovine and porcine skins and bones. However, in the light of bovine spongiform encephalopathy and foot-and-mouth disease, the use of collagen and collagen-derived products derived from cattle and pigs has been called into question. No evidence suggests, however, that viral or subviral infectious particles adapted to cold-blooded organisms can be transmitted to humans.

Fish skins and bones are high in collagen, as are the exoskeletons (shells) of crustaceans such as lobster, crab, shrimp, and crawfish. The processing of fin fish and shellfish generates a great deal of waste that contains high collagen levels. The discharged materials are not only unused, but their discharge generally entails disposal fees or other costs for the seafood processor. There has not previously been an economical method to extract and purify collagen from such sources.

Most methods that have previously been reported for the extraction of collagen from fish skin have employed the use of ethylenediaminetetraacetic acid (EDTA). However, the U.S. Food and Drug Administration has not approved the use of EDTA for collagen to be used in food and cosmetics applications.

To the knowledge of the inventors, there have been no prior reports of any methods for extracting collagen from calcified tissue (e.g., fish skin with scales, alligator skeletons, chicken skeletons, crustacean shells, bones, cartilage, egg shells) that have not employed a decalcification step to remove calcium from the tissue prior to the extraction of collagen. The ability to extract collagen from calcified tissue without a prior decalcification step would provide greater flexibility.

The ability to extract collagen from fish skin without the use of EDTA would be advantageous, as it could lead to quicker acceptability of the resulting product for food or cosmetic uses.

Fish scales are high in calcium. It has previously been thought that a preliminary decalcification step was needed before extracting collagen from calcified tissues such as fish bones or fish scales. In prior techniques for extracting collagen from fish skin, the skin has usually been descaled, or has come from fish that have only small scales in the first place. The ability to extract collagen from fish skin that contains substantial quantities of scales, without the need to first remove scales from the skin would be a substantial advantage.

Takai, U.S. Pat. No. 5,698,228 discloses a skin substitute comprising a sheet of squid chitin as a substrate and a laminar layer of fish skin collagen laid on the substrate. In an example at col. 4, line 41 through col. 5, line 45, salmon skin is employed in a collagen extraction method. The extraction process included acetic acid treatment, followed by pepsin, dialysis and salting out, re-dissolving in acetic acid, dialysis, and freeze-drying. Although it was not clearly stated whether the salmon skin was or was not descaled, salmon have only very small scales anyway, and salmon skin has only low levels of calcium.

Huc, U.S. Pat. No. 5,331,092 discloses the preparation of collagen using calf skin as the starting material. At col. 2, line 60 through col. 3, line 6, is disclosed a biological decontamination treatment performed prior to acidifying the collagenic tissue. A preferred biological decontamination treatment was treatment in a soda bath, preferably a soda bath around 1 N.

Shimizu, U.S. Pat. No. 6,271,350 describes a process for producing fish collagen. Scales were removed from salmon skin as part of the pretreatment. See col. 3, lines 39–41. The patent states that prior methods of producing fish skin collagen had used an organic solvent such as ethanol to remove non-collagen substances from the skin, including proteins, fats, and oils. Disadvantages of ethanol treatment are mentioned. See Col. 1, lines 42–62. The disclosed process (col. 2, lines 5–20) included admixing a salt with raw fish skin, and leaving the skin mixed with the salt in a cold condition for degreasing and deodorization; removing the salt from the skin along with non-collagen substances; extracting collagen from the de-salted skin; and filtering the collagen portion to remove non-collagen substances such as fats, oils, odors, and colors.

Taylor, U.S. Pat. No. 5,703,211 discloses the preparation of collagen from fish isinglass (swim bladders). As compared to prior methods of doing so, a step of pre-drying the isinglass was avoided, for example by freezing it. It was mentioned that the isinglass could be hydrolyzed to solubilize the collagen. Typically, hydrolysis was conducted under acid (pH 1.5 to 5) or alkaline (pH 8 to 13) conditions. See col. 2, lines 33–47.

Devictor, U.S. Pat. No. 5,420,248 discloses the extraction of collagen from unpigmented fish skin—e.g., the ventral skin of flatfish. It was said that the pigment from pigmented fish skin was difficult to remove, and therefore unpigmented fish skin was used. The ventral skin was said to be available, already scaled, in large quantities. Col. 2, lines 11–17. Collagen was then extracted with acid, and precipitated with salt.

Visser, European Patent Application 1 270 672 discloses the extraction of collagen from animal hides or skin, such as porcine and bovine skins, preferably porcine skins. When the collagen is separated from an acidified suspension, it is disinfected, preferably with hydrogen peroxide, alkali metal hypochlorite, or ozone. See paragraph [0022] of the publication.

J. Kim et al, "Application of ozone for enhancing the microbiological safety and quality of foods: a review," *J. Food Prot.*, vol. 62, pp. 1071–1087 (1999) (abstract) discloses the use of ozone as a disinfectant to enhance the microbiological safety of a variety of food products. The authors reported that ozone is generally recognized as safe (GRAS), and that ozone had been used with mixed success to inactivate contaminant microflora on meat, poultry, eggs, fish, fruits, vegetables, and dry foods. Additional research was said to be needed to optimize the use of ozone in food applications.

There is an unfilled need for a method to extract collagen from calcified tissue without employing a prior decalcification step.

There is an unfilled need for improved methods to extract collagen from fish skin without the use of EDTA for decalcification.

There is an unfilled need for a method to extract collagen from fish skin that contains substantial quantities of scales, without the need to first remove scales from the skin.

We have discovered a method to extract collagen from calcified tissue without employing a prior decalcification step. The method may be used with calcified tissues such as fish skin with scales, alligator skeletons, and crustacean exoskeletons. It does not require the use of EDTA. When fish skin is used that contains substantial quantities of scales, it is not necessary first to remove scales from the skin before conducting the extraction of collagen.

The novel process for extracting collagen from calcified tissue containing collagen employs the following steps. These steps should occur consecutively, except that steps (a) and (b) may be performed in either order, or simultaneously.
(a) treating the tissue with an aqueous alkali solution, in a concentration and for a time sufficient to remove at least some non-collagen protein from the tissue;
(b) treating the tissue with alcohol, in an amount and for a time sufficient to dissolve at least some odoriferous substances from the tissue, and then separating the alcohol from the tissue;
(c) rinsing the tissue with water, in an amount and for a time sufficient to bring the pH of the tissue between about 7 and about 8;
(d) treating the tissue with an aqueous solution of acid and pepsin, in concentrations and for a time sufficient to dissolve at least some collagen from the tissue into the aqueous solution;
(e) filtering the mixture of tissue and aqueous solution, to separate the aqueous solution with dissolved collagen from the undissolved tissue components;
(f) dissolving salt in the filtered aqueous solution containing dissolved collagen, in a concentration and for a time sufficient to cause at least some of the collagen to precipitate from the aqueous solution; and
(g) collecting the precipitated collagen.

The novel process is further characterized in that, prior to the step of treating the tissue with the aqueous solution of acid and pepsin, no substantial decalcification of the tissue occurs; and in that the process does not employ ethylenediaminetetraacetic acid (EDTA).

The use of ozonated water in the various steps of the process is preferred, as the ozone both kills microorganisms, and oxidizes trace compounds that might otherwise generate undesirable odors. Ozone ($O_3$) is generally recognized as safe (GRAS) because, among other things, it degrades into diatomic oxygen ($O_2$).

Some of the process steps may optionally be repeated, as discussed further in connection with the example given below.

BRIEF DESCRIPTION OF THE DRAWING

The single drawing is a flow chart that depicts schematically an embodiment of the process of the present invention.

EXAMPLE

Following is a description of an example implementing the present invention. Unless otherwise stated, the process steps were carried out at 15° C. The same example is depicted schematically in the flow chart shown in the accompanying FIGURE.

Step I. Alkaline treatment of fish skin. One hundred pounds (45 kg) of black drum (*Pogonias cromis*) and sheepshead seabream (*Archosargus probatocephalus*) fish skin with scales were obtained from a south Louisiana seafood processing facility. The skin with the scales was cut into pieces and suspended in 200 liters of ice-cold, ozonated water containing 1.76 pounds (800 g) of sodium hydroxide for one day with gentle stirring. The alkaline extract (supernatant) was drained using a basket with 1 cm×1 cm mesh. The skin was resuspended in 200 liters of ice-cold, ozonated water containing 1.76 pounds (800 g) of sodium hydroxide for one additional day of gentle stirring. The alkaline extract (supernatant) was then drained. The alkaline treatment is believed to eliminate a number of other, unwanted proteins from the starting materials.

Step II. Alcohol treatment of the skin. The skin was then covered with ethanol for at least 5 hours. The alcohol was drained off. The recovered alcohol is preferably recycled for future use, e.g., by distillation. The ethanol treatment is believed to dissolve various odoriferous substances. Because ethanol denatures proteins, including collagen, it was surprising that this step could be conducted with a food grade ethanol, rather than with another alcohol such as isopropanol, which would be less likely to denature proteins but that would tend to leave an unpleasant odor and that is not generally recognized as safe. The denaturation could be avoided by conducting this step at a cool temperature. In prototype experiments, this step was conducted at about 7° C.

Step III. Washing or Rinsing. The skin was then washed with 200 liters of ice-cold, ozonated water several times (at least three times), until the pH of the washing solution reached a pH between about 7 and about 8. The rinsing returned the skins to a neutral (or near-neutral) pH prior to the acid treatment step. The ozone treatment is believed to oxidize various odoriferous substances, as well as to kill microbes.

Step IV. First extraction of Collagen using Acid and Pepsin. The skin was then suspended in 200 liters of ice-cold, ozonated water containing 6 liters of glacial acetic acid and 0.44 pounds (200 g) pepsin. The contents were stirred for 3–5 days, until the suspending liquid became viscous. (Longer stirring periods increased overall yield.) The acid extracts collagen from the starting materials. The treatment with pepsin cleaves a portion of the collagen molecule, increasing the yield obtained by the acid extraction by several-fold.

Step V. Filtration. The skin was then filtered using a three-part filtration. In the first part, a pet screen was used; in the second part a super solar screen was used, and in the third part, a 105 micron polypro screen was used. The filtrate (filtered fraction) was saved for the isolation of a first collagen fraction, sometimes called "1st collagen," following steps VI-b through the Final Step, as described further below. The retentate (skin containing scales) was used to conduct second and third extractions of collagen (sometimes called "2nd collagen" and "3rd collagen"), as described further in Step VI-a below.

Step VI-a. Second extraction of Collagen with Acid and Pepsin. The retained fraction (skin containing scales) from step V was suspended in 152 liters of ozonated, ice-cold water to which had been added 4.6 liters of glacial acetic acid and 0.44 pounds (200 g) pepsin. The mixture was then allowed to sit for 4 days, as otherwise described in step IV. Then, the mixture was filtered as otherwise described in step V above to yield a 160-liter filtrate, and a retained fraction (retentate). The filtrate (filtered fraction) was treated following steps VI-b through the Final Step, as described further below to generate "2nd collagen." The retentate (skin containing scales) was used for a third isolation of collagen using acid and pepsin, as otherwise described in step IV, after which it was filtered, as otherwise described in step V. The filtered solution (filtered fraction) was treated following steps VI-b through the Final Step, as described further below, to generate the "3rd collagen," which was very white in color (whiter than the 1st and 2nd collagens, with a higher degree of purity).

Step VI-b. Salting-out. Twenty pounds (9 kg) sodium chloride was dissolved into the filtered fraction (approximately 160 liters each) from each of step V or the two repetitions of step VI-a. A white precipitate then appeared in the solution. The mixture was then left unstirred for 3 h or overnight. The salting-out precipitated the collagen from solution.

Step VII-b. Dehydration. The white precipitate was filtered out with a screen, and the resulting crude solid collagen was squeezed to drain excess liquid.

Step VII-b. Solubilization, Salting-out, and Dehydration. The solid collagen was re-dissolved in 160 liters of ozonated, ice-cold water containing 1.2 liters of glacial acetic acid. About 20 pounds (9 kg) of pure sodium chloride was added to 26 liters of ozonated, ice-cold water, and the resulting solution was added to the 200 liter solution containing collagen and acetic acid. After standing overnight, the mixture was drained through a 105 micron polypro screen and a super solar screen. The resulting solid collagen was squeezed to drain excess liquid. Step VIII-b (solubilization, salting-out, and dehydration) is optionally repeated to increase the purity of the collagen.

Final step. The collagen was dissolved in a mixture of 20 liters of ozonated, ice-cold water and 0.2 liters of glacial acetic acid using an agitator. The pH of the solution was between pH 3 and 4. Depending on the intended end use, the collagen may be maintained in the acidic solution, or it may be lyophilized to produce a solid product.

The collagen produced was a functional, non-denaturing, type-II collagen, with high molecular weight (ca. 340 kDa, as measured by SDS-PAGE). Although testing is still underway, it is believed that the collagen product produced by this process is highly pure, and is hypoallergenic, making it suitable for use in food, cosmetic, and pharmaceutical applications. The 1st collagen contained traces of gray particles from fish skin, the 2nd collagen contained very few traces, and the 3rd collagen was essentially free from any of the gray particles. The overall yield of the entire process was about 30%. The purity of the 3rd collagen was about 95.5%. We expect that further purification through centrifugation will yield 99+% pure collagen.

Optional step. We also found that rubbing the fish skin with titanium dioxide improved the whiteness of the collagen after the first extraction. In one example, frozen fish skin was thawed, cut into pieces, dipped into 0.1 N NaOH at pH 8.5, and then rubbed with 1% (w/w) $TiO_2$ for 24–48 h at 4° C. The extraction was otherwise conducted as previously described. The resulting collagen was substantially whiter, and had substantially fewer gray spots than resulted from an otherwise similar treatment without the $TiO_2$ step.

Miscellaneous

The process as described above has also been successfully used to extract collagen from chicken skeletons and alligator skeletons. The processes were substantially identical to those described above for extraction from fish skin. However, there is little benefit to using $TiO_2$ with chicken skeleton or alligator skeleton, since the gray spots we observed in extractions from fish skin were not seen.

As used in the specification and claims, unless context clearly indicates otherwise, a "calcified" tissue refers to a collagen-containing biological tissue or organ that comprises a substantial concentration of calcium. A "calcified" tissue may have calcium integrally intermingled throughout the tissue (e.g., bone or egg shell), or the calcium may be present in isolated pieces of tissue, but still be present in a sufficiently high overall concentration (e.g., the scales attached to a piece of fish skin). For example, recent tests conducted on our behalf determined that salmon skin had a calcium level of about 8,251 ppm, while black drum contained about 240,767 ppm. The latter would be considered to be a "calcified" tissue within the scope of this definition, while the former would not. Numerically, a calcified tissue may be said to be one that has a calcium level of about 20,000 ppm or greater, preferably about 50,000 ppm or greater, and more preferably about 100,000 ppm or greater.

The complete disclosures of all references cited in this specification are hereby incorporated by reference. Also incorporated by reference are the complete disclosures of the following publications and unpublished manuscripts, each of which presents, in pertinent part, the work of the present inventors: M. Ogawa et al., "Biochemical properties of bone and scale collagens isolated from the subtropical fish black drum (*Pogonia cromis*) and sheepshead seabream (*Archosargus probatocephalus*)," *Food Chemistry*, vol. 88, pp. 495–501 (2004); M. Ogawa et al., "Biochemical properties of black drum and sheepshead seabream skin collagen," *J. Agric. Food Chem.*, vol. 51, pp. 8088–8092 (2003); M. Ogawa et al., "Bone and scale collagens from subtropical fish black drum and sheepshead seabream: biochemical and thermal (physicochemical) properties," submission to *Food Chemistry* or *International Journal of Biological Macromolecules* (2003); M. Ogawa et al., "Biochemical properties of collagen from skin of Gulf coast fish," Abstract 76A-33, presented at Annual Meeting of the Institute of Food Technologists (Chicago, Ill., Jul. 12–16, 2003); J. Losso et al., "Two value-added products from Louisiana seafood processing facilities," *Louisiana Agriculture*, pp. 11–12 (Fall 2002); and "LSU researchers may create new industry from fish waste," *Sunday Advocate* (Baton Rouge, La.), p. 41 (Apr. 20, 2003); and A. Wood et al., "Biochemical properties of *Alligator mississippiensis* bone," Summer Undergraduate Research Forum Paper #95, Louisiana Biomedical Research Network, (Baton Rouge, La., Jul. 31, 2003). In the event of an otherwise irreconcilable conflict, however, the present specification shall control.

What is claimed:

1. A process for extracting collagen from calcified tissue containing collagen, said process comprising the steps of:
   (a) treating the tissue with an aqueous alkali solution, in a concentration and for a time sufficient to remove at least some non-collagen protein from the tissue;

(b) treating the tissue with ethanol, in an amount and for a time sufficient to dissolve at least some odoriferous substances from the tissue, and then separating the alcohol from the tissue;

(c) rinsing the tissue with water, in an amount and for a time sufficient to bring the pH of the tissue between about 7 and about 8;

(d) treating the tissue with an aqueous solution of acid and pepsin, in concentrations and for a time sufficient to dissolve at least some collagen from the tissue into the aqueous solution;

(e) filtering the mixture of tissue and aqueous solution, to separate the aqueous solution with dissolved collagen from the undissolved tissue components;

(f) dissolving salt in the filtered aqueous solution containing dissolved collagen, in a concentration and for a time sufficient to cause at least some of the collagen to precipitate from the aqueous solution; and (g) collecting the precipitated collagen;

wherein:

prior to the step of treating the tissue with the aqueous solution of acid and pepsin, no substantial decalcification of the tissue occurs;

and wherein:

said process does not employ ethylenediaminetetraacetic acid (EDTA);

and wherein:

steps (a) through (g) occur consecutively in the order listed above; except that steps (a) and (b) may occur in either order, or steps (a) and (b) may occur concurrently.

2. A process as recited in claim 1, wherein at least some of the water or some of the aqueous solutions are ozonated.

3. A process as recited in claim 1, wherein all the water and all the aqueous solutions are ozonated.

4. A process as recited in claim 1, wherein said alkali treating step is repeated at least twice prior to said alcohol treating step.

5. A process as recited in claim 1, wherein said water rinsing step is repeated a sufficient number of times to bring the pH of the tissue between about 7 and about 8.

6. A process as recited in claim 1, wherein said collecting step comprises the step of at least partially dehydrating the precipitated collagen.

7. A process as recited in claim 6, additionally comprising the step, after said dehydrating step, of dissolving the precipitated collagen in an aqueous acidic solution.

8. A process as recited in claim 7, additionally comprising, after said acidic dissolving step, repeating sequentially said steps of precipitating the dissolved collagen with salt, collecting and dehydrating the precipitated collagen, and dissolving the precipitated collagen in an aqueous acidic solution.

9. A process as recited in claim 1, additionally comprising repeating steps (d) through (g) with the undissolved tissue components remaining after filtering step (e), to extract additional collagen from the tissue.

10. A process as recited in claim 1, wherein all the water and all the aqueous solutions are ozonated; and wherein said alkali treating step is repeated at least twice prior to said alcohol treating step; and wherein said water rinsing step is repeated a sufficient number of times to bring the pH of the tissue between about 7 and about 8; and additionally comprising the step, after said dehydrating step, of dissolving the precipitated collagen in an aqueous acidic solution; and additionally comprising, after said acidic dissolving step, repeating sequentially said steps of precipitating the dissolved collagen with salt, collecting and dehydrating the precipitated collagen, and dissolving the precipitated collagen in an aqueous acidic solution; and additionally comprising repeating steps (d) through (g) with the undissolved tissue components remaining after filtering step (e), to extract additional collagen from the tissue.

11. A process as recited in claim 1, wherein the calcified tissue comprises tissue selected from the group consisting of fish skin with scales, alligator skeleton, chicken skeleton, turkey skeleton, crustacean shell, bone, cartilage, and egg shell.

12. A process as recited in claim 1, wherein the calcified tissue comprises fish skin with scales.

13. A process as recited in claim 1, wherein the calcified tissue comprises alligator skeleton.

14. A process as recited in claim 1, wherein the calcified tissue comprises chicken skeleton.

15. A process as recited in claim 1, wherein said ethanol treating step is conducted at about 7° C.

16. A process as recited in claim 1, wherein the calcified tissue comprises fish skin with scales; and wherein said process additionally comprises the step of rubbing the fish skin with $TiO_2$ for a time sufficient to improve the whiteness of the resulting collagen produced by the process, as compared to the whiteness of collagen that is produced by a process that is otherwise identical, but that lacks the $TiO_2$-rubbing step.

* * * * *